US005823196A

United States Patent [19]

Harasymiw

[11] Patent Number: 5,823,196

[45] Date of Patent: Oct. 20, 1998

[54] METHOD FOR DETECTING ALCOHOL CONSUMPTION RATES

[76] Inventor: James W. Harasymiw, 127 Balmoral Ct., Brookfield, Wis. 53005

[21] Appl. No.: 669,836

[22] Filed: Jun. 26, 1996

Related U.S. Application Data

[63] Continuation of Ser. No. 275,101, Jul. 14, 1994, abandoned.

[51] Int. Cl.[6] .................... A61B 19/00

[52] U.S. Cl. .................... 128/898; 436/71; 436/66

[58] Field of Search .................... 128/898, 923; 364/400, 401; 436/71, 66; 514/811

[56] References Cited

U.S. PATENT DOCUMENTS

| | | | |
|---|---|---|---|
| 4,463,098 | 7/1984 | Hoberman | 436/67 |
| 4,770,996 | 9/1988 | Tabakoff | 435/18 |
| 4,814,280 | 3/1989 | Peterson | 436/128 |
| 4,975,581 | 12/1990 | Robinson et al. | 250/339 |
| 5,066,583 | 11/1991 | Mueller | 435/18 |
| 5,126,271 | 6/1992 | Harasymiw | 436/71 |

OTHER PUBLICATIONS

Effects of alcohol intake on plasma fatty acids assessed independently of diet and smoking habits, Burke, V., Croft, K.D., Puddey, I.B., Cox, K.L., Beilin, L.J. and VanDongen, R., *Clinical Science* (1991), pp. 785–791.

Alcohol Consumption, Blood Alcohol Level and the Relevance of Body Weight in Experimental Design and Analysis, Devgun, M.S., and Dunbar, J.A., *Journal of Studies on Alcohol,* vol. 51, No. 1, 1990, pp. 24–28.

Biomedical Consequences of Alcohol Use and Abuse, Special Section, Alcohol and Health IV, *Alcohol Health and Research World,* (Spring 1981), pp. 10–31.

Patterns of Alcohol Consumption, Special Section, Alcohol and Health IV. *Alcohol Health and Research World,* (Spring, 1981), pp. 2–7.

Discriminant Function Analysis of Clinical Laboratory Data Use in Alcohol Research, Dolinsky, Z.S., and Schnitt, J.M., *IV* Markers for Risk of Alcoholism and Alcohol Intake,* Chapter 21, pp367–383.

Dimished Blood Selenium Levels in Alcoholics, Dworkin, B.M., Rosenthal, W.S., Gordon, G.G., and Jankowski, R.H., *Alcoholism: Clinical and Experimental Research,* Nov./Dec. 1984, pp 535–538.

Improved Separation of Acetaldehyde–Induced Hemoglobin, Hazlett, S.E, Liebelt, R.A. and Truitt, Jr., E.B., *Alcoholism: Clinical & Experimental Research,* vol. 17, 1993 (accepted for publication, page numbers not available).

Acetaldehyde–modified hemoglobin as a marker of alcohol consumption: Comparison of two new methods, Sillanaukee, P., Seppa, K. Koivula, T., Israel, Y. and Niemela, O., *Journal of Laboratory and Clinical Medicine,* Jul., 1992, pp. 42–47.

Effect of Acetaldehyde on Hemoglobin: $HbA_{1ach}$ as a Potential Marker of Heavy Drinking, Sillanaukee, P., Seppa, K. and Koivula, T., *Alcohol,* vol. 8, 1991 pp 377–381.

Correlation of Self–Administered Alcoholism Screening Test With Hemoglobin–Associated Acetaldehyde, Peterson, C.M., Ross, S.L., and Scott, B.K., *Alcohol,* vol. 7, 1991, pp. 289–293.

Improved Test of Hemoglobin–Acetaldehyde Adduct for Measuring Compliance with Alcoholism Treatment, Truitt, Jr., E.B., Hazelett, S.E. and Liebelt, R.A., unpublished article, document included.

Increased Blood Acetate: A New Laboratory Marker of Alcoholism and Heavy Drinking, Korri, U., Nuutinen, H. and Sataspuro,M., *Alcoholism: Clinical and Experimental Research,* Sep./Oct. 1985, pp468–471.

Elevated Blood Acetate as Indicator of Fast Ethanol Elimination in Chronic Alcoholics, Nuutinen, H., Lindors, K., Hekali, P. and Salaspuro, M., *Alcohol,* vol. 2, 1985, pp 623–626.

A New Approach to Quantitate Carbohydrate–Deficient Transferin Isoforms in Alcohol Abusers: Partial Iron Saturation in Isoelectric Focusing/Immunoblotting and Laser Densiometry, Bean, P. and Peter, J.B., *Alcoholism: Clinical and Experimental Research,* vol. 17, No. 6, 1993, pp 1163–1170.

Carbohydrate–Deficient Transferrin (CDT) as Indicator of Alcohol Misuse: Evaluation of Problems in the Methodology, Girela, Eloy, Hernandez–Cueto, Claudio and Villaneuva, Enrique, source unknown, document included.

Carbohydrate–Deficient Transferrin (CDT): A New Tool for Monitoring Alcohol Abuse, Maryland Medical Laboratory, Inc. *Techline,* vol. 2, No. 2, Feb., 1993.

Carbohydrate deficient transferrin: a marker for alcohol abuse, Kapur, A., Wild, G., Milford–Ward, A. and Triger, D.R., *British Medical Journal,* Aug., 1989, pp427–431.

Mechanism and Significance of Carbohydrate Intolerance in Chronic Alcoholism, Sereny, G. and Endrenyi, L., *Metabolism,* vol. 27, No. 9, Sep. 1978, pp 1041–1046.

Carbohydrate–Deficient Transferrin in Serum: a New Marker of Potentially Harmful Alcohol Consumption Reviewed, Stibler, H., *Clinical Chemistry,* vol. 37, No. 12, 1991, pp 2029–2037.

(List continued on next page.)

*Primary Examiner*—Mickey Yu
*Assistant Examiner*—Kelly O'Hara
*Attorney, Agent, or Firm*—Reinhart, Boerner, Van Deuren Norris & Rieselbach, S.C.

[57] ABSTRACT

A method for assessing or determining alcohol consumption rates including using a blood specimen from a human subject to develop an individual blood constituent panel; comparing the individual panel with a reference blood constituent panel to provide categories corresponding to rates of alcohol consumption; and identifying the category of consumption rate. The methods of the invention can be varied through modification of one of several statistical models used therewith to preferentially weigh the analysis and identify one consumption category over another. Multivariate and similar such statistical techniques correlate comparisons of individual/subject blood and reference panel constituents with recognized consumption rates.

21 Claims, No Drawings

OTHER PUBLICATIONS

Studies on the Association Between Alcohol and High Density Lipoprotein Cholesterol: Possible Benefits and Risks, Cauley, J.A., Kuller, L.H., LaPorte, R.E., Dai, W.S. and D'Antonio, J.A., *Advances in Alcohol & Substance Abuse,* vol. 6(3), Spring 1987, pp 53–67.

Plasma and red cell lipids in alcholics with macrocytosis, Clemens, M.R., Kessler, W., Schied, H.W., Schupmann, A. and Waller, H.D., *Clinica Chimica Acta,* 156 (1986), pp. 321–328.

Alcohol: High Density Lipoproteins, Apolipoproteins, Cushman, Jr., P. Barboriak, J. and Kalbfleisch, J., *Alcoholism: Clinical and Experimental Research,* vol. 10, Mar./Apr. 1986, pp. 154157.

Alcohol and high–density lipoproteins, Devenyi, P., Robinson, G.M. and Roncari, D.A.K., *CMA Journal,* Nov. 22, 1980, vol. 123, pp 981–984.

Alcohol Consumption and High Density Lipoprotein Cholesterol Concentration among Alcoholics, Dai, W.S., LaPorte, R.E., and Hom, D.L., Kuller, D'Antonio, J.A., Gutai, J.P., Wozniczak, M. and Wohlfahrt, B., *American Journal of Epidemiology,* vol. 122, No. 4, 1985, pp 620–627.

Biochemical and Hematological Correlates of Alcoholism, Ryback, R.S., Eckhardt, M.J. and Pautler, C.P., *Research Communications in Chemical Pathology and Pharmacology,* vol. 27, No. 3, Mar. 1980, pp 533–550.

Hematological Concomitants of Alcoholism: Development and Validation of a Clinical Screening Technique, Hawkins, M.R., Silsby, H.D., Druzich, D.J. and Sittig, D.R., *Journal of Substance Abuse Treatment,* vol. 1, 1984, pp 271–276.

Biochemical Markers for Alcoholism: Chan, A.W.K., *Children of Alcoholics: Critical Perspectives,* 1990, pp 311–329.

Biochemical Markers for Alcoholism: Sensitivity Problems, Cushman, P., Jacobson, G., Barboraik, J.J. and Anderson, A.J., *Alcoholism Clinical and Experimental Research,* vol. 8, No. 3, May/Jun. 1984, pp. 253–256.

Biologic–Marker Studies in Alcoholism, T. Reich, *The New England Journal of Medicine,* Jan. 21, 1988, pp 180–182.

Biological Correlates and Detection of Alcohol Abuse and Alcoholism, M.J. Eckardt, R.R. Rawlings and P.R. Martin, *Neuro–Psychopharmacology & Bio. Psychiat.,* vol 10, 1986, pp 135–144.

Effects on Abstinence on the Ability of Clinical Laboratory Tests to Identify Male Alcoholics, M.J. Eckardt, R.R. Rawlings, R.S. Ryback, P.R. Martin and L.A. Gottschalk, *American Journal of Clinical Pathology,* Sep., 1984, pp 305–310.

Biochemical Markers of Alcohol Consumption, A.S. Rosman and C.S. Lieber, *Alcohol Health & Research World,* vol. 14, No. 3, 1990, pp. 210–218.

Utility and Evaluation of Biochemical Markers of Alcohol Consumption, A.S. Rosman, *Journal of Substance Abuse,* 4, 1992, pp 277–297.

The Effectiveness of Biologic Markers to Diagnose Alcoholism, R.S. Ryback, R.R. Rawlings, G.L. Negron, R. Correa–Coronas, D. Cirelli and S.Cjhobanian, *Controversies in Alcoholism and Substance Abuse,* 1986, pp 191–207.

Biochemical Tools in Alcohol Research, C.S. Lieber, *Alcohol Health & Research World,* vol 14, No. 3, 1990, pp 193–196.

Clinical Diagnostic Techniques and Assessment Tools in Alcohol Research, S.A. Maisto and G.J. Connors, *Alcohol Health & Research World,* vol. 14, No. 3, 1990, pp 232–238.

Serum alanine aminotransferase levels among volunteer blood donors: effect of sex alcohol intake and obesity, N. Bizzaro, F. Tremolada, C. Casarin, P. Bonetti, F. Noventa, G. Diodati, C. Drago and G. Realdi, *Italian Journal of Gastroenterology,* 1992:24, pp 237–241.

Serum Zinc, Copper, and Ceruloplasmin Levels in Male Alcoholics, C. Wu, J. Lee, W.W. Shen and S. Lee, *Biological Psychiatry,* vol. 19, No. 9, 1984, pp 1333–1338.

Serum copper and zinc in random samples of the population of Northern Ireland, D. McMaster, E. McCrum, C.C. Patterson, M. McF Kerr, D. O'Reilly, A.E. Evans, and A. HG Love, *American Journal of Clinical Nutrition,* 1992:56, pp 440–446.

Serum apolipoprotein A–II, a biochemical indicator of alcohol abuse, P. Puchois, M. Fontan, J. Gentilini, P. Gelez, J. Fruchart, *Clinica Chemica Acta,* 1984, pp 185–189.

Differences in Platelet Enzyme Activity between Alcoholics and Nonalcoholics, B. Tabakoff, P.L. Hoffman, J.M. Lee, T. Saito, B. Willard and F. De Leon–Jones, *The New England Journal of Medicine,* Jan. 21, 1988, pp 134–139.

Carbohydrate–deficient Transferrin, a Marker for Chronic Alcohol Consumption in Different Ethnic Populations, U.J. Behrens, T.M. Womer, L.F. Braly, F. Schaffner, and C.S. Lieber, *Alcoholism: Clinical and Experimental Research,* vol. 12, No. 3, May/Jun. 1988, pp 427–432.

Sex–related differences in the haematological effects of excessive alcohol consumption, D.M. Chalmers, I. Chanarin, S. MacDermott and A.J. Levi, *Journal of Clinical Pathology,* 33:1980, pp 3–7.

Alcohol–Related Hospitalizations of Elderly People, W.L. Adams, Z. Yuan, J.J. Barboriak, A.A. Rimm, *Journal of the American Medical Association,* Sep. 8, 1993, vol 270, No. 10, pp 1222–1225.

Average, Binge and Maximum Alcohol Intake in Healthy Young Men: Discriminant Function Analysis, R. Cowan, L.K. Massey and T.K. Greenfield, *Journal of Studies on Alcohol,* vol. 46, No. 6, 1985, pp 467–472.

Detection of the Relationship between Moderate Alcoholic Beverage Consumption and Serum Levels of Estradiol in Normal Postmenopausal Women: Effects of Alcohol Consumption Quantitation Methods and Sample Size Adequacy, J.S. Gavaler and K. Love, *Journal of Studies on Alcohol,* vol. 53, No. 4, 1992, pp 389–394.

Use of Laboratory Tests to Monitor Heavy Drinking by Alcoholic Men Discharged from a Treatment Program, M. Irwin, S. Baird, T.L. Smith and M. Schukit, *American Journal of Psychiatry,* 145:5, May 1988, pp. 595–599.

Subj: Perspectives on Alcoholism Treatment, G.R. Jacobson, Technical Comments submitted to *Science,* Apr. 1987, pp 1–13.

Detection, Assessment and Diagnosis of Alcoholism, Current Techniques, publication unknown, document included G.R. Jacobson, pp 377–408.

Estimation of Blood Alcohol Concentrations in Young Male Drinkers, *Alcoholism: Clinical and Experimental Research,* vol. 15, No. 3, pp 494–499.

The Epidemiology of Alcohol Consumption, L. T. Midanik and R. Room, *Alcohol, Health & Research World,* vol 16, No 3, pp 183–190.

Alcoholism Detection Markers in Blood Samples of Road Users, M. Staak and R. Iffland, *Japanese Journal of Alcohol & Drug Dependence,* 27(1), 1992, pp 42–49.

CDT by Anion–Exchange Chromatography Followed by RIA as a Marker of Heavy Drinking Among Men, P. Sillanaukee, K. Seppa, K. Lof and T. Koivula, *Alcoholism: Clinical and Experimental Research,* vol 17, No 2, 1993, pp 230–233.

Excessive Consumption of Alcohol in Men as a Biological Influence Factor in Clinical Laboratory Investigations, D. Stamm, E. Hansert and W. Feuerlein, *Journal of Clinical Chemistry Clinical Biochemistry,* vol 22, 1984, pp 65–77.

Alcohol, Women and Heart Disease, J. Doria, *Alcohol & Research World,* vol 14, No 4, pp 349–351.

Serum Carbohydrate–Deficient Transferrin as a Marker of Alcohol Consumption in Patients with Chronic Liver Diseases, H. Bell, C. Tallaksen, T. Sjaheim, R. Weber, N. Raknerud, H. Orjasaeter, K. Try and E. Haug, *Alcoholism: Clinical and Experimental Research,* vol 17, No. 2, pp. 246–252.

Low Blood Selenium Levels in Alcoholics With and Without Advanced Liver Disease, B. Dworkin, W.S. Rosenthal, R.H. Jankowski, G.G. Gordon and D. Haldea, *Digestive Diseases and Sciences,* vol 30, No 9, Sep. 1985, pp. 838–844.

The Relationship between liver function tests and alcohol intake in patients admitted to an Alcoholism Unit, J.R. Evans, S. Ogston, A. Guthrie, B. Johnston and L. McKechnie, *Annals of Clinical Biochemistry,* 1984, 21: pp 261–267.

Markers of Chronic Alcohol Ingestion in Patients with Nonalcoholic Steatohepatitis: An Aid to Diagnosis, L.M. Fletcher, I. Kwoh–Gain, E.E. Powell, L.W. Powell and J.W. Halliday, *Hepatology,* vol 13, No 3, 1991, pp 455–459.

Decreased serum selenium in alcoholics as related to liver structure and function, H. Korpela, J. Kumpulainen, P.V. Luoma, A.J. Arranto and E.A. Sotaniemi, *American Journal of Clinical Nutrition,* 42, Jul. 1985, pp 147–151.

Variations in HDL and VLDL levels chronic alcoholics, Influence of the degree of liver damage and of withdrawal of alcohol, S. Tateossain, J.G. Peynet, A.G. Legrand, B. Collet, J.A. Rossignol, J.J. Delattre and F.J. Rousselet, *Clinica Chimica Acta,* 148, 1985, pp 211–219.

Discriminant Analysis and Clustering, Panel on Discriminant Analysis, Classification and Clustering, *Statistical Science,* vol 4, 1989, pp 34–69.

METHOD FOR DETECTING ALCOHOL CONSUMPTION RATES

This is a continuation of application Ser. No. 08/275,101 filed on Jul. 14, 1994 now abandoned.

BACKGROUND OF THE INVENTION

This invention is related generally to methods for evaluating individuals in terms of their rates of alcohol consumption and, more particularly, a method for identifying and/or screening those individuals of a larger population whose consumption rates indicate problematic behavior and/or alcoholic tendencies.

Alcoholism is a serious human health issue and it has been predicted that it will affect about 16% of the population. Mortality rates among alcoholics are two to three times the rate for the general population and it has been suggested that it is one of the leading preventable causes of death, injury, illness and impaired functioning. In 1994, the National Institute on Alcoholism and Alcohol Abuse cited reports estimating the total societal costs for alcoholism in 1993 of about $140 billion dollars. Considerable effort has been directed toward the development of techniques for diagnosing alcoholism or excessive consumption rates. One technique involves the examination of blood serum variables, while the remaining three are psychological assessments.

An example of earlier work based on examination of blood serum variables is described in a paper titled "Biochemical and Hematological Correlates of Alcoholism" by Ryback et al., published in *Research Communications in Chemical Pathology and Pharmacology.* Vol. 27, No. 3, Mar. 1980. The authors considered a number of blood serum constituents in several combinations. Best accuracy (86% in the combined alcoholic group) resulted when they used the SMA 12 (12 standard constituents), SMA 6 (6 standard constituents) and Hematological (7 standard constituents) tests in combination. Table 2 of the paper shows the 25 total constituents. The authors experienced 16% false negatives, i.e., 16% of the alcoholics were identified as being nonalcoholics. No false positives were experienced.

Two aspects of the Ryback et al. paper are particularly important. One is that the prior probabilities (a reflection of apparent historical fact) used by the authors were 0.5 for medical controls, 0.4 for treatment program alcoholics and 0.1 for alcoholics admitted to medical wards. These values were selected arbitrarily but were influenced by a study which indicated that about 50% of a group of patients admitted to a Veterans Hospital had alcohol related problems.

The authors further indicate that adjustment of the prior probabilities by + or −0.1 resulted in no significant change in the accuracy of the discrimination between alcoholics and nonalcoholics. They also stated that "[t]he prior probabilities could be changed from 0.4 to 0.8 in the medical controls and from 0.6 to 0.2 in the alcoholics with no significant change in the accuracy of discrimination." The other particularly important aspect of the Ryback et al. paper is a quotation appearing on page 545. There, the authors state that "[s] ignificant relationships involving drinking variables were observed for all tests except cholesterol . . ." (emphasis added).

Another relevant paper dealing with examination of blood serum variables is titled "Hematological Concomitants of Alcoholism: Development and Validation of a Clinical Screening Technique" by Hawkins et al., published in *Journal of Substance Abuse Treatment,* Vol. 1, 1984. While the age and sex of the subjects were noted, no observation was made as to whether such factors are of use in identifying abuse. Hawkins et al. used two different multi-variate discriminant analyses which yielded classification accuracies significantly different from one another. The quadratic analysis correctly classified about 94% of alcoholics while the stepwise analysis correctly classified about 79% of alcoholics. The authors' caveat states ". . . This technique is unlikely to provide sufficiently precise classification for anything other than medical screening purposes, which should then be bolstered with independent substantiation before arriving at a diagnosis."

Some of the earlier work involving analysis of blood serum variables considers the blood chemistry constituents selenium and magnesium. Such work is described in a paper titled "Diminished Blood Selenium Levels in Alcoholics" by Dworkin et al. published in *Alcoholism: Clinical and Experimental Research,* Vol. 8, No. 6, Nov./Dec. 1984. The authors have noted that alcoholics have a reduced level of selenium. As stated in the Abstract, this fact is of concern to the authors "[s]ince selenium deficiency can produce a spectrum of organ injury . . . the relationship of selenium deficiency to alcohol-induced organ injury deserves further study."

Clearly, the subjects had already been identified as alcohol abusers—the focus of the research was prospective organ damage. And the authors observe that low selenium levels can also result from diet, cancer, severe burns and kwashiorkor. In other words, a low selenium blood serum level per se was not appreciated as having value in the diagnosis of alcohol abuse. A similar paper is "Decreased Serum Selenium in Alcoholics as Related to Liver Structure and Function" by Korpela et al. published in *The American Journal of Clinical Nutrition,* Jul. 1985.

Other work involving blood serum variables is described in a paper titled "Serum Zinc, Copper, and Ceruloplasmin Levels in Male Alcoholics" by Wu et al. published in *Biological Psychiatry,* Vol. 19, No. 9, 1984. The authors used blood samples from known alcoholics having an average daily consumption level of about 294 mL of absolute alcohol. They noted the reciprocal relationship between serum zinc and copper levels and found that the serum zinc level in alcoholic patients was lower than that of a control group. While the serum copper level was higher, the authors indicate it was a not statistically significant. The authors also observe that earlier workers have found a psychiatric condition, i.e., depression, to be associated with lower serum zinc levels and low zinc, copper and ceruloplasmin levels. In an added note, the authors also state, with respect to serum levels of calcium and magnesium, that "[t]heir differences were not statistically significant between alcoholics and controls."

Yet another paper dealing with blood serum variables is titled "Alcohol Consumption and High Density Lipoprotein Cholesterol Concentration Among Alcoholics" by Dai et al. published in *American Journal of Epidemiology,* Vol. 122, No. 4, 1985, wherein findings are presented indicating a largely inconclusive relationship of HDL cholesterol levels and consumption rates: HDL cholesterol increased with increasing alcohol consumption up to about 450 mL of ethanol consumption per day, then decreased or appeared to decrease The authors primarily examined the relationship between alcohol consumption and the level of HDL subclasses HDL2 and HDL3.

Currently, most persons suspected of having a drinking problem are screened using psychological tests, some of which are mentioned below. A drawback to reliance on such tests to the exclusion of other considerations is that their results depend heavily upon the subject's good will, i.e., information as voluntarily disclosed by the subject, as well as other subjective criteria such as personality, demeanor, appearance, and the like. Because denial is a common trait among alcoholics, various manifestations of the denial syndrome can skew the test results to the detriment of an accurate assessment/diagnosis.

One widely-used psychological approach, empirical in nature, is known as the McAndrew scale of the Minnesota MultiPhasic Personality Inventory (MMPI). The McAndrew scale is representative of other similar approaches and generally accepted as a reliable method of alcohol assessment. It has been demonstrated to correctly classify about 84% of alcoholics when a cutoff score of 24 raw points is used. There are about 10 false negatives and 14 false positives using such cutoff point.

In general, the McAndrew test is composed of those items from the MMPI to which alcoholics respond differently than does the general population. The subject is required to respond to "true" or "false" questions which include latent "check" questions to detect whether the subject has answered consistently. It should be noted, however, that the accuracy of the McAndrew scale has come into question because it also seems to respond to other non-alcohol forms of drug addiction, as well as to general deviancy.

Irrespective of the approach or method used, it should be appreciated that when tests are used for certain purposes, e.g., screening job applicants, false positives present a certain risk for the tester. The subject/applicant may be denied employment, promotion, or personal advancement if s/he is falsely identified as a heavy drinker or alcoholic. Ryback et al. euphemistically refers to this happenstance as "clinically embarrassing." In more practical terms, it can give rise to actual and/or legal liability.

Another psychological approach involves the use of consumption pattern questionnaires. The Khavari Alcohol Test is an example of such an approach. In studies of validity and reliability, the Khavari test has consistently and relatively accurately differentiated between alcoholic and control groups. The Khavari test considers the drinking patterns of individuals (as provided by such individuals) and compares such patterns with established statistical drinking norms. These comparisons are then used for making diagnostic decisions.

Yet another psychological approach involves a variety of questionnaires which attempt to count incidents of problems or behaviors thought to be symptomatic of alcoholism. The Michigan Alcoholism Screening Test (MAST), and the National Council on Alcoholism Criteria for the Diagnosis of Alcoholism (CRIT) are examples. In a modified form known as MODCRIT, the latter is used clinically.

U.S. Pat. Nos. 3,954,409 (HSIA), 3,645,688 (Smernoff), 4,115,062 (Morre et al.), 4,820,628 (Weitz), 4,753,890 (Smith-Lewis et al.), 4,820,647 (Gibbons) and 4,837,164 (Glick) describe methods of analyzing blood serum constituents. Such patents do not suggest how such methods might be used for determining the consumption rate of alcohol or for diagnosing alcoholism.

The Smernoff and Hsia patents involve cholesterol in blood and describe methods for recognizing the type and presence of hyperlipoproteinemia (Smernoff) or for assessing the risk of coronary heart disease (Hsia). The Smith-Lewis et al. patent describes a method for determining magnesium ions in, among other things, blood serum and plasma. While the patent says the determination of such ion can be used for diagnosing and treating various ailments, alcohol consumption/abuse is neither mentioned nor suggested.

On the other hand, there are situations where a false positive causes little or no adversity to anyone but the risk of a false negative is relatively great. For example, alcoholism in persons under consideration for alcoholism treatment should be identified with a relatively high level of certainty. Another example involves selection of persons for highly sensitive tasks requiring, e.g., certain unusual physical skills or a high level of confidentiality. The public interest in selection accuracy may be sufficiently high so as to outweigh considerations of adversity arising from a false positive. In those instances, the sole question is not how much the subject is drinking but whether s/he is drinking alcoholically. Identification of such individuals is enhanced by using only two prior rather than three probability values: 0.5 and 0.5 rather than the more typical 0.9 and 0.1 Ryback values.

The prior art may be summarized by observing that it fails to appreciate how the actual level or rate (within somewhat broad ranges) at which an individual is consuming alcohol can be relatively quickly determined by analyzing the serum variables in a blood sample taken from such individual. A method for making such a determination while minimizing false positive results would be an important advance in identifying individuals having problematic consumption rates and, in the extreme cases, diagnosing alcoholism. This is especially true if the level of accuracy is sufficient to permit the method to be the sole or at least predominant, clinical diagnostic tool.

OBJECTS OF THE INVENTION

It is an object of this invention to provide an improved method for determining the rate of consumption of alcohol which overcomes the problems, limitations and shortcomings of the prior art.

Another object of this invention is to provide a non-subjective method for determining the rate of consumption of alcohol such that any evaluation or assessment is objective.

Yet another object of this invention is to provide an improved method for identifying categories of alcohol consumption which can serve as a singular, or at least predominant, tool in diagnosing problematic alcohol-related behavior.

Another object of this invention is to provide an improved method for determining rates of alcohol consumption rate which is efficient, economical and easily used in combination with standard blood work.

Another object of this invention is to provide a method for identifying categories of alcohol consumption which can be used with equal effect in conjunction with, and without limitation, pre-employment screening, post-accident assessment, chemical drug trials to, inter alia, indicate alternative treatment approaches or concurrent drug abuse and pre-prescription diagnosis of potential drug interaction.

Another object of this invention is provide a method for identifying and/or assessing alcohol consumption levels with or without correlation to daily ingestion volumes, notwithstanding periods of abstinence.

Another object of this invention is to provide a method which can be used in conjunction with standard and/or widely-used alcohol markers, such that they are used selectively and more effectively as part of a reflex test to confirm a given consumption category and/or minimize false positive results.

Another object of the present invention is to provide a method for identifying alcohol consumption categories which utilize a previously-compiled base of blood panels and/or blood work up results, notwithstanding the circumstances under which the blood samples, panels, and/or results were obtained.

Another object of the invention is to provide a method for use in conjunction with one of several statistical techniques which permits manipulation of standard reference panels and individual/subject panels to determine a minimum number of panel constituents or combination of a minimal number of constituents and/or other factors which can be utilized to meet accuracy, sensitivity, and other-related performance criteria, with or without subsequent reflex testings Another object of this invention is to provide a method for use in conjunction with one of several statistical techniques to predict a categorical outcome.

Another object of this invention is to provide a method for use in conjunction with one of several statistical techniques, such that panel constituents are not analyzed and/or compared merely on the basis of abnormalities, but also by consideration intra-panel constituent relationships.

Another object of the invention is to provide a method for use in conjunction with one of several statistical techniques, such that accuracy is increased by incorporation of non-constituent factors into the analysis and/or comparison.

Another object of the invention is to provide a method which permits adjustment of prior probabilities such that the analysis can be tailored to preferentially identify a particular consumption category.

Another object of the invention is to provide a method which permits adjustment of prior probabilities such that the analysis is tailored to preferentially minimize false positive identifications.

Another object of the invention is to provide a method for determining a category of alcohol consumption rate which accounts for inter-laboratory differences, equipment variations, and related analytic anomalies.

Another object of the invention is to provide a method for determining a category of alcohol consumption rate which involves, in part, correlation of subject and reference blood constituent panels with consumption rate categories derived from one of a variety of alcohol assessment standard instruments.

These and other important objects will be apparent from the following description and examples.

SUMMARY OF THE INVENTION

This invention is an improved method for the assessment of alcohol consumption, which provides a means to evaluate and determine an individual's rate of alcohol intake, in a manner which minimizes false positive results without a necessarily concomitant loss in sensitivity. The method can be varied through modification of a statistical model used therewith to preferentially weigh the analysis and identify one consumption category over another. Multi-variate and similar such statistical techniques correlate comparisons of individual/subject blood and reference panel constituents with recognized consumption rate categories.

In accordance with the present invention, a method for assessing alcohol consumption rates includes (1) using a blood specimen from a human subject to develop an individual blood constituent panel, which has about at least ten constituents; (2) comparing the individual panel with a reference blood constituent panel to provide categories corresponding to rates of alcohol consumption; and (3) identifying the category of consumption rate for the subject indicated by the comparison. The reference blood constituent panel includes value ranges for the level of each constituent, whereby the relationship of one constituent to another can be determined. The reference panel is developed using a pool of human subjects and priority probability values corresponding to the likelihood that the subject would be classified in a particular category of alcohol consumption. A plurality of alcohol consumption categories are available for correlation to the reference panel, the number of categories depending upon the alcohol assessment standard instrument employed.

In preferred embodiments of the invention, three categories of alcohol consumption are used in conjunction with the reference panel. In highly preferred embodiments, a probability value of about 0.7–0.9 represents the lowest consumption rate; a probability value of about 0.08–0.20 represents the intermediate consumption rate; and a probability value of about 0.01–0.10 represents the highest consumption rate.

As mentioned above, consumption rate categories are derived from alcohol assessment standard instruments. Instruments useful with the present invention include psychological tests such as the Khavari Alcohol Test, the McAndrew scale, and MODCRIT. In highly preferred embodiments, the standard instruments are volume frequency alcoholism assessment tests.

The method of this invention can further include use of a statistical analysis which is modifiable to preferentially identified to one category of consumption rate over another. In preferred embodiments, the analysis is a multi-variate statistical technique. In highly preferred embodiments, the technique is selected from the group consisting of logistic regression, discriminant analysis, cluster analysis, factor analysis, and neuronetworking. The preferred technique includes standardization of individual/subject constituent panels through conversion of detected constituent levels to standard scores, to account for inter-facility/laboratory differences. The accuracy of the method is further increased where the individual and reference panels and statistical analysis incorporate such factors as age, gender, race, nationality, diet, geography, socio-economic status, and drug interaction.

The method of this invention can include a second comparison of an individual panel with a reference panel having β-hexacosanamine (Betahex) such that the category of consumption rate can be identified without false positive results. Additional reference panel constituents includes selenium, carbohydrate deficient transferrin, and hemoglobin associated acetaldehyde, among others.

The present invention also includes a method for determining the approximate rate of alcohol consumption by a human test subject, having the steps (1) using a blood specimen from a subject to develop a subject blood constituent panel having at least 12 constituents, two of which are high density lipoprotein and magnesium; (2) comparing the subject panel with a first reference constituent panel to provide categories corresponding to rates of alcohol consumption, the reference panel including high density lipoprotein and magnesium as constituents; (3) identifying the category of consumption rate for the subject indicated by the comparison; and (4) comparing, where the subject is identified with a particular category of alcohol consumption rate, the subject panel with a second reference constituent panel including β-hexacosanamine as an additional constituent, such that false positive results are minimized. The reference blood constituent panel includes value ranges corresponding to the level of each constituents, whereby the relationship of one constituent to another can be determined. The reference panel is developed using a pool of human subjects and prior probability values corresponding to the likelihood that the subject would be classified in a particular category of alcohol consumption. A plurality of alcohol consumption categories can be employed. In preferred embodiments, three categories of alcohol consumption, corresponding to increase consumption rates of alcohol per unit tine, are used and associated with prior probability values of about 0.70–0.90 for that category reflecting the lowest consumption rate, about 0.08–0.20 for that category reflecting the intermediate consumption rate, and about 0.01–0.10 for that category reflecting the highest consumption rate.

The categories of alcohol consumption are derived from alcohol assessment standard instruments. In preferred embodiments, the instruments are volume frequency alcoholism assessment tests. In highly preferred embodiments, the assessment tests are selected from the group consisting of the Khavari Alcohol Test, the McAndrew Scale, and MODCRIT.

The method of the invention can further include use of a statistical analysis modifiable to preferentially identify one category of consumption rate over another. In highly preferred embodiments, the analysis is a multi-variate statistical technique. In highly preferred embodiments, the technique is a statistical model such as logistic regression, discriminant analysis, cluster analysis, factor analysis, and neuronetworking. The accuracy of the method is enhanced by incorporating into the panels and statistical analysis factors such as age, gender, race, nationality, diet, geography, socioeconomic status and drug interaction.

As mentioned above and with general regard to the invention, the persons used to develop the reference panel of the present invention are preliminarily grouped into one of two classification variables related to alcohol consumption, i.e., abusive and non-abusive categories. Groups are derived through use of a psychological test, preferably selected from a group of such tests including the Khavari Alcohol Test, the McAndrew scale and MODCRIT. Of these, the Khavari Alcohol Test is a preferred assessment instrument.

The accuracy of the invention is improved where the reference panel is developed using a relatively large number of subjects—typically, at least several hundred subjects and preferably about 1200 or more subjects. The resulting reference blood serum panel may include any of the widely-recognized SMA 6, SMA 12 and Hematological constituents although other similar, common tests and their corresponding constituents may also be used to develop such a reference panel. Still other embodiments of the present method involve development of reference and individual/subject panels, ranges of age, individual/subject gender and like factors to further enhance accuracy.

As noted above, the present invention includes a method for determining an individual's alcohol consumption level based upon certain blood constituents (or variables as they are sometimes called) and upon the levels of such constituents compared to a reference. The constituents are collectively known as a panel i.e., a listing of constituents such as glucose, albumin, red blood count and the like which are present (as detected by lab laboratory analysis) in blood serum. For a given blood sample, each constituent is accompanied by an indication of the level of such constituent (usually per unit of volume) present in the sample. Of course, each constituent can—and does—vary from person to person and from time to time for a particular person. As a result, so-called normal ranges recognize the possibility of such variations. The reference panel includes not only the normal range of values for each serum constituent but also includes at least two other ranges for each constituent. These additional ranges relate to "heavy" and "very heavy" consumption rates of alcohol.

The reference and individual/subject panels include, alternatively, at least ten or at least twelve constituents, wherein two of the twelve are HDL and magnesium. But for the inclusion of HDL and magnesium with respect to the second alternative, the precise constituent makeup of either panel is not especially critical. For example, many laboratories offer blood serum analysis services and provide their own panel construction. A variety of blood serum constituents can comprise either panel, the identity and number of which are limited only by their response, and accuracy thereof to the general level of alcohol consumption, their relationship one to another, and the analytic capabilities of an individual laboratory. The constituent response to either alcohol consumption or to another constituent, is not necessarily linear and, in most instances, is distinctly non-linear.

Constituents useful with the method of the present invention include but are not limited to neurophils-platelet type (BASO), calcium (Ca), chlorine (Cl), direct bilirubin (DBIL), lactose dehydrogenase (LDH), monophils-platelet type (MONO), sodium (Na), phosphorus (P), white blood count (WBC), copper (Cu), and zinc (Zn), among others. Blood constituents useful with the methods of this invention are generally alcohol-specific; that is, they are less affected by other events occurring in the body than they are by the level and/or rate of alcohol consumption.

One embodiment of the invention includes high density lipoprotein and magnesium as constituents. The blood serum level of HDL increases with heavy drinking while that of magnesium decreases. Selenium, copper and/or zinc are additional constituents. In general, the levels of selenium and zinc decline with heavy alcohol consumption, while the level of copper increases. Selenium is also useful as a constituent for the purpose of a second comparison of an individual panel with a reference panel to eliminate false positive results. Other constituents used with the same effect include β-hexacosanarnine, carbohydrate deficient transferrin, and hemoglobin associated acetaldehyde. While the prior art uses the last two constituents as part of tests purporting to be alcohol markers, the present invention can utilize them much more effectively, not by themselves, but as a part secondary comparison or reflex test off the reference panel. Considerable cost savings are realized by using such constituents primarily to eliminate false positives from a given alcohol consumption category identified through an initial screening or comparison.

The reference panel used with a method of the invention is derived from persons, taken from populations having, by percent distribution, known drinking habits, grouped preliminarily into one of two classification variables, i.e., abusive, consumer and non-abusive consumer categories, using one of several available alcohol assessment standard instruments. Notwithstanding accepted test methodology, a formerly-abusive consumer is grouped into the non-abusive consumer category only if s/he had been abstinent for at least 8 weeks rather than the customary 2–3 weeks.

Preferred assessment instruments include psychological tests such as the Khavari Alcohol Test, the McAndrew scale and MODCRIT. Of this group, the Khavari test is most preferred. A feature of the Khavari test is that it elicits information from the subject which enables annual consumption rates of alcohol to be closely estimated. Annual consumption of ethanol is organized according to three groupings, one of which becomes the second classification variable described above. The Khavari test also includes check questions which aid greatly in assessing respondent veracity.

Under the constricts of the Khavari test, consumption of 0–590 oz. ethanol annually comprises Group 3, light-to-moderate; consumption of 591–1180 oz. annually comprises Group 2, moderate-to-heavy; consumption of more than 1180 oz. annually comprises Group 1, very heavy. The consumption rates represent one, two and more than two standard deviations above the mean, respectively.

After all alcohol consumers in the panel population are identified and categorized as described above, blood samples are taken from each person in each group and analyzed. Correlation of each sample (and its analysis) to the relevant group i.e., Group 3, 2 or 1, is maintained so that the reference norms are accurately related to the group responsible for the data.

Consistent with the comparative methodology of the invention, prior probability values can be assigned from categorization in Group 3, 2 or 1, and preferred values are between about 0.7 and 0.9, between about 0.08 and 0.20 and between about 0.01 and 0.10 for groups 3, 2 and 1, respectively. Within those ranges, prior probability values of about 0.86, 0.1 and 0.04, respectively, are highly significant. Such values correspond to the chances that a person belongs in a particular group, and are consistent with the level of alcohol consumption in the general population. Such values are useful in broad application of the present invention as a diagnostic tool by business, institutions and care providers.

The member panels comprising the reference blood serum panel can be treated with a multi-variate statistical technique to provide weighted values for each constituent of the reference panel. As shown in the Examples below, discriminant analysis is a preferred statistical technique, although others can be used with comparable results without deviating from the scope of this invention. Discriminant analysis can be performed through use and with the aid of the DISCRIM computer program, from the Statistical Package For Social Science (SPSS) PC+ statistical package available from SPSS, Inc. of Chicago, Ill. However, other statistical programs are also available for use with discriminant analysis, as well as with other statistical and/or multi-variate techniques suitable for use with the invention.

Discriminant analysis is a technique commonly used in the social sciences and less frequently in medicine. It is similar to logistic regression in that it can be used to predict a nominal or categorical outcome. Discriminant analysis differs from logistic regression in several ways; most importantly: it assumes that the independent variables follow a multi-variate normal distribution, so that it must be used with caution if some X variables are nominal; and it can be used with a dependent variable that has more than two values.

The procedure involves determining several discriminant functions, which are nothing more than linear combinations of the independent variables, that separate or discriminate among the groups to the extent possible. The number of discriminant functions needed can be determined by a multi-variate test statistic referred to as Wilks' Lambda. The discriminant functions' coefficients can be standardized, then interpreted in the same manner as with multiple regression to draw conclusions about which variables are important in discriminating among the groups. See, also, Dawson-Saunders and Trapp, *Basic and Clinical Biostatistics,* published by Appleton & Lange; and Altman, *Practical Statistics for Medical Research,* published by Chapman & Hall, both of which are incorporated herein, in their entirety, by reference.

The result is a standardized (canonical discriminant functions' coefficients) reference blood serum panel which provides reference ranges for each constituent and for each of the three consumption levels, i.e., light-to-moderate, moderate-to-heavy and very heavy. A method consistent with the invention may further include gender, age and the like categories as additional variables to further enhance accuracy of the method. Typical age categories are 18–35, 36–64 and over 64 years of age. After the reference panel is developed, it is used in comparison with an individual/subject panel, which is preferably constructed like the reference panel, with respect to constituent composition. The individual/subject panel is then statistically analyzed against the reference panel, with the deviations noted.

EXAMPLES OF THE INVENTION

The following non-limiting examples illustrate use of methods and identification of consumption levels, in accordance with the present invention. Comparisons of multiple individual/subject panels against a reference panel were simulated by random choice of a large member of individual data sets from a larger reference pool. Using this database (292, Examples 1 and 2; and 248, Example 3) 80% of the panels (240, Examples 1 and 2; and 196, Example 3) were randomly selected to comprise reference norms (a different 240 for each of Examples 1 and 2), such that the remaining 20% of each served as a validation group of unknowns with which to evaluate the methodology employed. Comparison of the consumption category identified through use of a particular method with the category known for each individual panel of the validation group gave the percent correctly classified, as well as the false negatives and false positives.

Example 1

Using a 10-constituent panel and prior probabilities of 0.3 and 0.7, the data sets of 292 males under age 36 were chosen, of which 240 comprised the reference panel and 52 were randomly selected, as described above. As shown in Tables 1a–1c and well-known to those skilled in the art and made aware of this invention, the discriminant functions were determined, with the coefficients standardized and assigned weighted values. Constituent levels are either directly or inversely proportional to consumption rates. A significance of 0.000 indicated that the odds the conclusions drawn about variables in discriminating among groups and the categorical outcome determined were the result of chance are less than one in ten thousand. In Table 1d the functions are evaluated at group means. The clustered array of group 1 centroids about 0.46860 and group 2 centroids about −1.96610 denotes a high degree of accuracy. One hundred percent of the non-abusive consumers and 79.1% of the abusive consumers were correctly identified, as a result of this analysis and subsequent comparison. Overall, 82.7% of the group cases were correctly identified, with zero false positive identifications.

TABLE 1a

Prior probabilities

| Group | Prior | Label |
|---|---|---|
| 1 | .30000 | Abusive |
| 2 | .70000 | Non-abusive |
| Total | 1.00000 | |

Canonical Discriminant Functions

| Fcn | Eigenvalue | Pct of Variance | Cum Pct | Canonical Corr | After Fcn | Wilks' Lambda | Chi-square | df | Sig |
|---|---|---|---|---|---|---|---|---|---|
| 1* | .9291 | 100.00 | 100.00 | .6940 | 0 | .518377 | 152.436 | 10 | .0000 |

*Marks the 1 canonical discriminant functions remaining in the analysis.

TABLE 1b

| Standardized canonical discriminant function coefficients | |
|---|---|
| | Func 1 |
| BASO | .16914 |
| CA | −.20721 |
| CL | .70725 |
| DBIL | .19026 |
| HDL | .49681 |
| LDH | −.37079 |
| MONO | .49334 |
| NA | −.64226 |
| P | .24934 |
| WBC | .45374 |

TABLE 1c

| Structure matrix: Pooled within-groups correlations between discriminating variables and canonical discriminant functions (Variables ordered by size of correlation within function) | |
|---|---|
| | Func 1 |
| HDL | .38860 |
| MONO | .38135 |
| P | .31358 |
| CA | −.31146 |
| CL | .26174 |
| DBIL | .23827 |
| NA | −.23366 |
| BASO | .12925 |
| LDH | −.10747 |
| WBC | .07452 |

TABLE 1d

Canonical discriminant function evaluated at group means (group centroids)

| Group | Func 1 |
|---|---|
| 1 | .46860 |
| 2 | −1.96610 |

Symbols used in plots

| Symbol | Group | Label |
|---|---|---|
| 1 | 1 | Abusive |
| 2 | 2 | Non-abusive |
| # | | All ungrouped cases |

All-groups Stacked Histogram
Canonical Discriminant Function 1

```
            32 +                                                          +
               |                                                          |
 F             |                            1                             |
 r          24 +                            1                             +
 e             |                         #  1 1                           |
 q             |                         2 11 1                           |
 u             |                         1 1111                           |
 e          16 +                         1 11111                          +
 n             |                        11111111    1                     |
 c             |                   2    11111111    1                     |
 y           8 +                  22 2 1111111111  11                     +
               |                 2222121111111111 11                      |
               |              2 2221111111111111111 11                    |
               |              22222111111111111111 111 1                  |
               |          22222222221111111111111111111111111    1        |
             X +----------+---------+---------+---------+---------+-------+ X
            out         -4.0      -2.0        .0       2.0       4.0       out
 Class          222222222222222222222222222222221111111111111111111111111111111
 Centroids                          2          1
```

TABLE 1e

| Actual Group | No. of Cases | Predicted Group Membership 1 | 2 |
|---|---|---|---|
| Classification results for cases selected for use in the analysis - | | | |
| Group 1 | 193 | 154 | 39 |
| Abusive | | 79.8% | 20.2% |
| Group 2 | 46 | 2 | 44 |
| Non-abusive | | 4.3% | 95.7% |
| Ungrouped cases | 1 | 1 | 0 |
| | | 100.0% | .0% |
| Percent of "grouped" cases correctly classified: 82.85% | | | |
| Classification results for cases not selected for use in the analysis - | | | |
| Group 1 | 43 | 34 | 9 |
| Abusive | | 79.1% | 20.9% |
| Group 2 | 9 | 0 | 9 |
| Non-abusive | | .0% | 100.0% |

Percent of "grouped" cases correctly classified: 82.69%

Example 2

As shown in Tables 2a–d and as described above, the discriminant functions were again determined with the coefficients standardized and assigned weighted values. A 10-constituent panel was again employed, with prior probabilities of 0.5 and 0.5 such that the analysis was weighted or slanted toward a population having a higher number of problem consumers, and away from sociological norm. The data sets of the same 292 males under age 36 were again chosen, of which 240 comprised the reference panel and 52 were randomly selected, with the result being that random selection produced a different group of 52 than that used for validation purposes in Example 1. Again, a significance of 0.0000 showed the analysis highly unlikely to be the result of chance. Subsequent comparison correctly identified 100% of the non-abusive consumers and 90.7% of the abusive consumers, with 92.3% overall correct identification and zero false positives.

TABLE 2a

Prior probability for each group is .50000
Canonical Discriminant Functions

| Fcn | Eigenvalue | Pct of Variance | Cum Pct | Canonical Corr | After Fcn | Wilks' Lambda | Chi-square | df | Sig |
|---|---|---|---|---|---|---|---|---|---|
| 1* | .9291 | 100.00 | 100.00 | .6940 | 0 | .518377 | 152.436 | 10 | .0000 |

*Marks the 1 canonical discriminant functions remaining in the analysis.

TABLE 2b

Standardized canonical discriminant functon coefficients

| | Func 1 |
|---|---|
| BASO | .16941 |
| CA | −.20721 |
| CL | .70725 |
| DBIL | .19026 |
| HDL | .49681 |
| LDH | −.37079 |
| MONO | .49334 |
| NA | −.64226 |
| P | .24934 |
| WBC | .45374 |

TABEL 2c

Structure matrix:
Pooled within-groups correlations between discriminating variables and canonical discriminant functions
(Variables ordered by size of correlation within function)

| | Func 1 |
|---|---|
| HDL | .38860 |
| MONO | .38135 |
| P | .31358 |
| CA | −.31146 |
| CL | .26174 |
| DBIL | .23827 |
| NA | −.23366 |
| BASO | .12925 |
| LDH | −.10747 |
| WBC | .07452 |

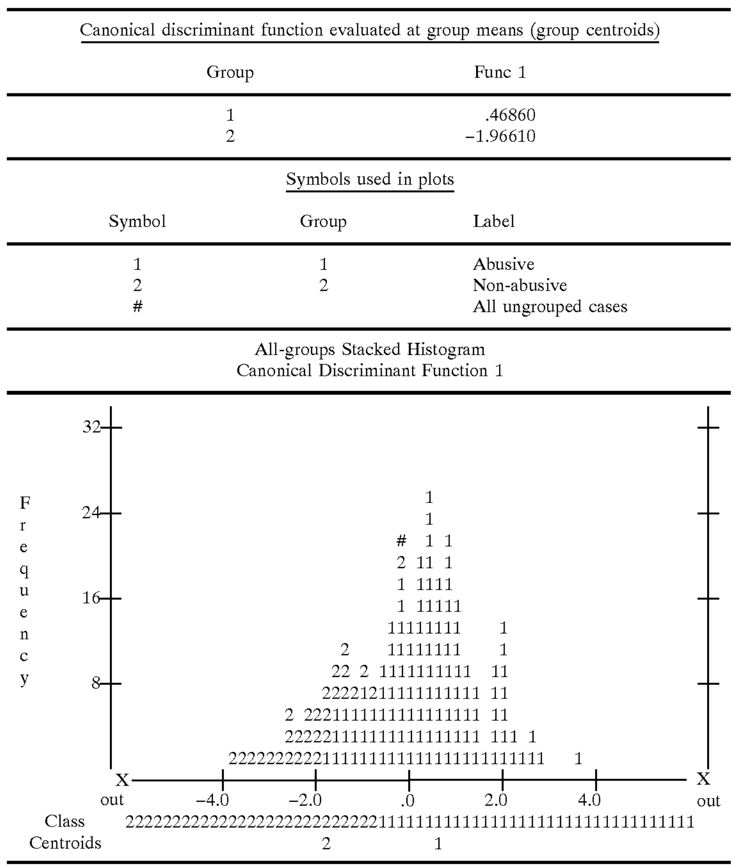

TABLE 2d

| Canonical discriminant function evaluated at group means (group centroids) | |
|---|---|
| Group | Func 1 |
| 1 | .46860 |
| 2 | −1.96610 |

Symbols used in plots

| Symbol | Group | Label |
|---|---|---|
| 1 | 1 | Abusive |
| 2 | 2 | Non-abusive |
| # | | All ungrouped cases |

All-groups Stacked Histogram
Canonical Discriminant Function 1

TABLE 2e

| Actual Group | No. of Cases | Predicted Group Membership 1 | 2 |
|---|---|---|---|
| Classification results for cases selected for use in the analysis - | | | |
| Group 1 | 193 | 167 | 26 |
| Abusive | | 86.5% | 13.5% |
| Group 2 | 46 | 3 | 43 |
| Non-abusive | | 6.5% | 93.5% |
| Ungrouped cases | 1 | 1 | 0 |
| | | 100.00% | .0% |
| Percent of "grouped" cases correctly classified: 87.87% | | | |
| Classification results for cases not selected for use in the analysis - | | | |
| Group 1 | 43 | 39 | 4 |
| Abusive | | 90.7% | 9.3% |
| Group 2 | 9 | 0 | 9 |
| Non-abusive | | .0% | 100.0% |

Percent of "grouped" cases correctly classified: 92.31%

Comparing Example 1 (prior probabilities of 0.3 and 0.7) and Example 2 (prior probabilities of 0.5 for each group) it is observed that a statistical analysis used in conjunction with a method of this invention can be modified to preferentially identify one category of consumption rate over another. While false positives were eliminated in each, the former was somewhat less sensitive. For certain uses and/or applications, such a decrease in sensitivity is acceptable where the prime consideration is the elimination of false positive results. As such, where identification of only those having alcoholic tendencies is required (for instance, prior probabilities of about 0.1 and 0.9) a slight decrease in sensitivity is acceptable so long as false positive indications are eliminated.

As noted above, the elimination of false positives is useful since blood serum analyses are often performed as part of, for example, a job application. The absence of false positives helps assure a user of the method that test results will not falsely indicate a person has a high rate of consumption when, in fact, s/he does not. Risk of loss of a job opportunity for reasons relating to alcohol consumption are thereby avoided.

Example 3

Another method in accordance with the present invention is illustrated below, with the comparisons made using the statistical analysis described in Examples 1 and 2. A reference panel of twelve constituents, including high density lipoprotein and magnesium, was formed by random selection of 80% of a selected number of cases, with the remainder (20%) as a validation group representing unknown individuals. Accuracy is, again denoted as above, with the tight cluster of centroids shown in Table 3a. The results show 90% (38 of 42) of the abusive drinkers were correctly identified in the validation group, with 20% (2 of 10) false positives; see Table 3b. To eliminate false positive results, all subjects which were identified as abusive drinkers (38 from Group 1 and 2 from Group 2) were retested and compared to a reference panel which included β-hexacosanamine (Betahex) as an additional constituent. Accuracy was again evident, as illustrated in Table 3b. Through the additional comparison/reflex test, 84% of the abusive consumers were correctly identified, with 0% false positives; see Table 3d. In a similar fashion, additional constituents such as selenium, hemoglobin associated acetaldehyde, and carbohydrate deficient transferrin can also be used as additional/reflex test constituents for the purpose of identifying a particular consumption category without false positive results.

TABLE 3a

All-groups Stacked Histogram
Canonical Discriminant Function 1

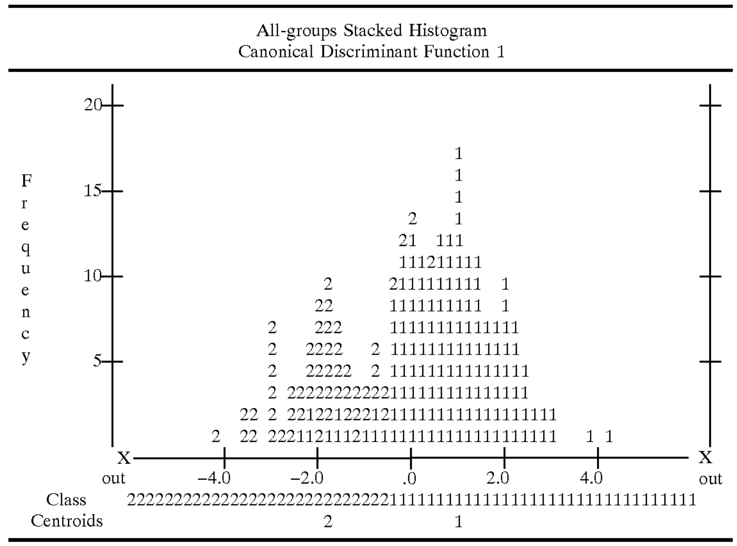

TABLE 3b

| Actual Group | No. of Cases | Predicted Group Membership 1 | 2 |
|---|---|---|---|
| Classification results for cases selected for use in the analysis - | | | |
| Group 1 | 134 | 126 | 8 |
| | | 94.0% | 6.0% |
| Group 2 | 61 | 3 | 58 |
| | | 4.9% | 95.1% |
| Ungrouped cases | 1 | 1 | 0 |
| | | 100.00% | .0% |

Percent of "grouped" cases correctly classified: 94.36%

| Classification results for cases not selected for use in the analysis - | | | |
|---|---|---|---|
| Group 1 | 42 | 38 | 4 |
| | | 90.5% | 9.5% |
| Group 2 | 10 | 2 | 8 |
| | | 20.0% | 80.0% |

Percent of "grouped" cases correctly classified: 88.46%

TABLE 3c

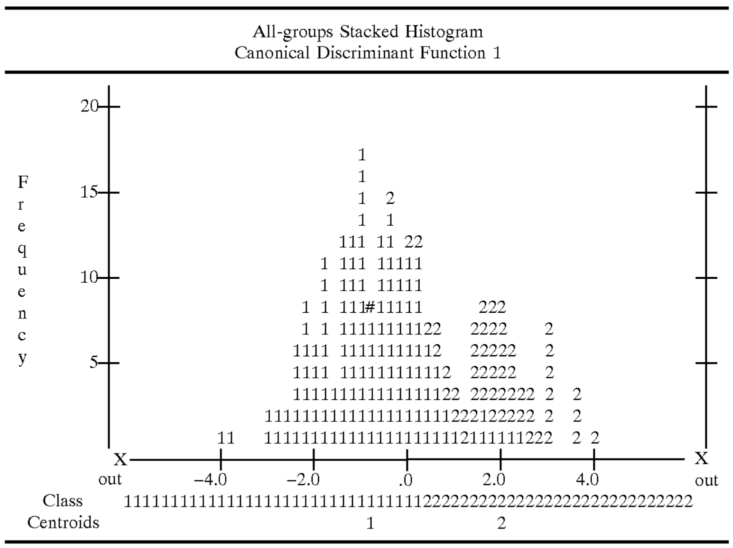

TABLE 3d

| Actual Group | No. of Cases | Predicted Group Membership 1 | 2 |
|---|---|---|---|
| Classification results for cases selected for use in the analysis - | | | |
| Group 1 | 134 | 117<br>87.3% | 17<br>12.7% |
| Group 2 | 61 | 2<br>3.3% | 59<br>96.7% |
| Ungrouped cases | 1 | 1<br>100.00% | 0<br>.0% |
| Percent of "grouped" cases correctly classified: 90.26% | | | |
| Classification results for cases not selected for use in the analysis - | | | |
| Group 1 | 38 | 35<br>92.1% | 3<br>7.9% |
| Group 2 | 2 | 0<br>0% | 2<br>100% |

While the principles of this invention have been described in connection with specific embodiments, it should be understood clearly that these descriptions are made only by way of example and are not intended to limit the scope of the invention, in any manner. For example, a constituent panel comprising a combination of less than ten constituents is contemplated, so long as accuracy, sensitivity, and false positive parameters are not unduly compromised. Likewise, other variables or factors, e.g. hormonal levels or patterns as a gender subfactor, can be used to enhance accuracy through use of the multi-variate statistical techniques described herein. In such a manner, incorporation of additional factors in conjunction with a reduced panel can also provide useful means for identification. Other advantages and features of the invention will become apparent from the claims hereinafter, with the scope of the claims determined by the reasonable equivalents as understood by those skilled in the art

What is claimed is:

1. A method of identifying individuals having a high alcohol consumption rate, said method comprising:

using a blood specimen from a subject to develop a subject blood constituent panel;

statistically analyzing said individual panel against a first reference panel;

identifying the category of consumption rate for said subject indicated by said analysis; and further analyzing said subject with a second reference blood constituent panel as a reflex test off said first reference panel, said second reference panel including an additional constituent, said additional constituent being a blood alcohol marker, whereby use of said second reference panel reduces the percentage of false positive results as compared to use of said first reference panel.

2. The method as defined in claim 1 wherein said reference blood constituent panel includes value ranges corresponding to the level of each said constituent, whereby the relationship of one constituent to another can be determined.

3. The method as defined in claim 2 wherein said subject panel constituent values are converted to standard scores.

4. The method as defined in claim 2 wherein said reference panel is developed using a pool of human subjects and prior probability values corresponding to the likelihood that said subject would be classified in a particular category of alcohol consumption.

5. The method as defined in claim 4 wherein there are a plurality of alcohol consumption categories, said categories corresponding to increasing alcohol consumption rates.

6. The method as defined in claim 5 wherein there are three categories of alcohol consumption, said categories corresponding to increasing consumption rates of alcohol per unit time.

7. The method as defined in claim 5 wherein said categories are derived from alcohol assessment standard instruments.

8. The method as defined in claim 7 wherein said instruments are volume frequency alcoholism assessment tests.

9. The method as defined in claim 8 wherein said instruments are selected from the group consisting of the Khavari Alcohol Test, the McAndrew Scale, and MODCRIT.

10. The method as defined in claim 1 wherein said comparison further includes use of a statistical analysis modifiable to preferentially identify one category of consumption rate over another.

11. The method as defined in claim 10 wherein said analysis is a multi-variate statistical technique.

12. The method as defined in claim 11 wherein said technique is selected from the group consisting of logistic regression, discriminant analysis, cluster analysis, factor analysis, and neuron networking.

13. The method as defined in claim 10 wherein said statistical analysis incorporates factors selected from the group consisting of age, gender, race, nationality, diet, geography, socioeconomic status and drug interaction to increase the accuracy of said identification.

14. A method of assessing alcohol consumption rates, comprising:

using a blood specimen from a human subject to develop an individual blood constituent panel;

statistically analyzing said individual panel against a reference panel, said analysis including setting prior probability values to preferentially identify a particular consumption rate;

determining said subject to have a particular consumption rate; and comparing said individual panel with a second reference panel having an additional constituent, said additional constituent selected from the group consisting of selenium, β-hexacosanamine, carbohydrate deficient transferrin, and hemoglobin associated acetaldehyde.

15. The method as defined in claim 14 wherein said analysis further includes determination and assignment of a weighted value for each panel constituent, said weighted value corresponding to a comparative statistical relationship of one constituent to another constituent.

16. The method as defined in claim 14 wherein said first reference panel is developed using a pool of human subjects and prior probability values corresponding to the likelihood that said subject would be classified in a particular category of alcohol consumption.

17. The method as defined in claim 16 wherein there are a plurality of alcohol consumption categories, said categories corresponding to increasing alcohol consumption rates.

18. The method as defined in claim 17 wherein said categories are derived from alcohol assessment standard instruments.

19. The method as defined in claim 14 further including use of statistical analysis modifiable to preferentially identify one category of consumption rate over another.

20. The method as defined in claim 19 wherein said analysis is a multivariate statistical technique.

21. The method as defined in claim 20 wherein said individual constituent panel is standardized.

* * * * *

UNITED STATES PATENT AND TRADEMARK OFFICE

CERTIFICATE OF CORRECTION

PATENT NO. : 5,823,196

DATED : October 20, 1998

INVENTOR(S) : James W. Harasymiw

It is certified that error appears in the above-identified patent and that said Letters Patent is hereby corrected as shown below:

Col. 2, Line 56: insert -- . -- after "decrease"

Col. 5, Line 3: Omit "testings" and insert -- testing. --

Col. 6, Line 60: Omit "tine" and insert -- time --

Col. 8, Line 20: Omit "hexacosanarnine" and insert -- hexacosanamine --

Signed and Sealed this

Twenty-eighth Day of December, 1999

Attest:

Q. TODD DICKINSON

Attesting Officer

Acting Commissioner of Patents and Trademarks